United States Patent
Mu et al.

(10) Patent No.: US 9,474,705 B2
(45) Date of Patent: Oct. 25, 2016

(54) METHODS COMPOSITIONS, AND KIT FOR WHITENING HYPER PIGMENTED SPOTS ON SKIN

(71) Applicant: ELC Management LLC, Melville, NY (US)

(72) Inventors: Weilin Mu, Albertson, NY (US); John R. Castro, Huntington Station, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 14/308,406

(22) Filed: Jun. 18, 2014

(65) Prior Publication Data

US 2014/0377198 A1    Dec. 25, 2014

Related U.S. Application Data

(60) Provisional application No. 61/836,701, filed on Jun. 19, 2013.

(51) Int. Cl.

| A61Q 19/02 | (2006.01) |
|---|---|
| A61K 8/89 | (2006.01) |
| A61K 8/58 | (2006.01) |
| A61K 8/81 | (2006.01) |

(52) U.S. Cl.
CPC .............. *A61K 8/585* (2013.01); *A61K 8/8152* (2013.01); *A61Q 19/02* (2013.01); *A61K 2800/74* (2013.01); *A61K 2800/95* (2013.01)

(58) Field of Classification Search
None
See application file for complete search history.

(56) References Cited

U.S. PATENT DOCUMENTS

| 3,439,088 A | 4/1969 | Edman |
| 3,818,105 A | 6/1974 | Coopersmith et al. |
| 4,584,355 A | 4/1986 | Blizzard et al. |
| 4,974,980 A * | 12/1990 | Gueret .................... B65D 51/32 401/119 |
| 5,103,812 A | 4/1992 | Salamone et al. |
| 5,236,986 A | 8/1993 | Sakuta |
| 5,412,004 A | 5/1995 | Tachibana et al. |
| 5,811,487 A | 9/1998 | Schulz, Jr. et al. |
| 5,837,793 A | 11/1998 | Harashima et al. |
| 5,899,622 A * | 5/1999 | Gueret ................. A45D 34/045 401/122 |
| 6,060,072 A | 5/2000 | Konik et al. |
| 6,183,593 B1 | 2/2001 | Narang et al. |
| 6,315,990 B1 | 11/2001 | Farer et al. |
| 7,014,844 B2 * | 3/2006 | Mahalingam ............ A61K 8/97 424/401 |
| 7,649,045 B2 | 1/2010 | Karpowicz et al. |
| 7,795,326 B2 | 9/2010 | Salamone et al. |
| 8,197,803 B2 | 6/2012 | Salamone et al. |
| 8,217,110 B2 | 7/2012 | Melancon et al. |
| 2004/0161395 A1 | 8/2004 | Patil et al. |
| 2004/0208839 A1 | 10/2004 | Leverett et al. |
| 2005/0196356 A1 * | 9/2005 | Leinen ..................... A61K 8/22 424/53 |
| 2006/0110346 A1 * | 5/2006 | Lu ............................ A61K 8/31 424/64 |
| 2007/0009446 A1 | 1/2007 | Romero |
| 2007/0253987 A1 * | 11/2007 | Wozniak .............. A61K 8/0245 424/401 |
| 2010/0203077 A1 | 8/2010 | Schnittger et al. |
| 2010/0239619 A1 * | 9/2010 | Hurwitz ............... A61K 8/0208 424/401 |
| 2011/0171149 A1 * | 7/2011 | Niki ........................ A61K 8/49 424/62 |
| 2011/0171288 A1 * | 7/2011 | Mohammadi ........ A61K 8/0295 424/450 |

FOREIGN PATENT DOCUMENTS

WO    WO-2004/024798    3/2004

OTHER PUBLICATIONS

Charkoudian, John C.; Polyken Technologies; A model skin surface for testing adhesion to skin; Journal of the Society of Cosmetic Chemists; 39; pp. 225-234; Jul./Aug. 1988.
Material Safety Data Sheet; Dow Corning Corporation; Dow Corning(R) BIO-PSA 7-4401 Silicone Adhesive; 9 pp; Jan. 2013.
Product Information; Healthcare; Dow Corning BIO-PSA; Standard Silicone Adhesives; BIO-PSA 7-4401; BIO-PSA 7-4501; BIO-PSA 7-4601; BIO PSA 7-4402; BIO-PSA 7-4502; BIO-PSA 7-4602; Silicone Adhesives; Non-sensitizing, Pressure Sensitive Adhesives; 4 pp.; Ref. No. 52-1052A-01; Jul. 2008.
Product Information; Healthcare; Dow Corning Soft Skin; Adhesives Parts A&B; Dow Corning MG 7-9800; Soft Skin Adhesive Kit (A&B); Dow Corning MG 7-9850; Soft Skin Adhesive Kit (A&B); Dow Corning MG 7-9900; Soft Skin Adhesive Kit (A&B); Ref. No. 52/1128-01; 4 pp; Jul. 2009.
International Search Report of ISA (KIPO) for PCT Application US2014/043002; mailing date: Oct. 27, 2014.
Written Opinion of ISA (KIPO) for PCT Application US2014/043002; mailing date: Oct. 27, 2014.

* cited by examiner

*Primary Examiner* — Abigail Fisher
(74) *Attorney, Agent, or Firm* — Julie Blackburn

(57) ABSTRACT

A skin whitening composition comprising a liquid polymeric coating material that, upon exposure to ambient air and moisture in skin, hardens to a water resistant, water vapor permeable, adherent and conformable solid film when applied to skin, and at least one skin whitening active; and a method and kit for whitening skin.

12 Claims, 1 Drawing Sheet

METHODS COMPOSITIONS, AND KIT FOR WHITENING HYPER PIGMENTED SPOTS ON SKIN

CROSS-REFERENCE TO RELATED APPLICATIONS

This application claims priority to U.S. provisional patent application Ser. No. 61/836,701 filed Jun. 19, 2013.

TECHNOLOGICAL FIELD

The invention is in the field of methods and compositions for use in whitening hyper pigmented spots on the skin.

SUMMARY OF THE INVENTION

As people age the skin undergoes many types of changes. One common change is the development of hyper pigmented spots on skin surfaces such as the face or hands. This can happen due to aging, sun exposure, or post-inflammation, the latter referred to as PIH or post-inflammatory hyper pigmentation.

A number of products exist for treating hyper pigmented skin, most commonly in the skin cream or lotion form. There are a number of difficulties in treating hyper pigmented spots on the hands, which is an area where they most commonly occur. One problem is that it is more difficult to apply the treatment cream to the hyper pigmented spot itself. When the cream is applied to the hands in general, the entire surface to which the cream is applied will be whitened, not just the hyper pigmented spot. The second problem is that cream applied to the hands wears off rather quickly due to hand washing, exposure to environment, and so on. Thus, there is a need for more effective ways to apply a skin whitening active directly to the hyper pigmented spot to be treated, have it remain on the spot for an effective period of time, and ideally, to have the treatment product mask the hyper pigmented spot while the treatment is ongoing.

The invention is directed to a composition, method and kit for application to hyper pigmented skin spots which remains on the spot for an extended period of time even after hand washing or exposure to environmental conditions such as rain, wind, etc., and optionally, that blends into the skin while the treatment is taking place.

The invention is directed to a skin whitening composition comprising a liquid polymeric coating material that hardens to a water resistant, water vapor permeable, adherent and conformable solid film when applied to skin, and at least one skin whitening active.

The invention is also directed to a method for whitening hyper pigmented spots on a skin treatment area comprising applying to the hyper pigmented spot a composition comprising a liquid polymeric coating material that hardens to a water resistant, water vapor permeable, adherent and conformable solid film when applied to skin, and at least one skin whitening active.

A kit for whitening hyper pigmented spots on skin comprising:

A receptacle having a closure and an applicator, and stored within the receptacle a liquid polymeric coating material that, upon exposure to ambient air and moisture in skin, will harden to a water resistant, water vapor permeable, adherent and conformable solid film when applied to skin, and at least one skin whitening active.

DETAILED DESCRIPTION

Figure 1:
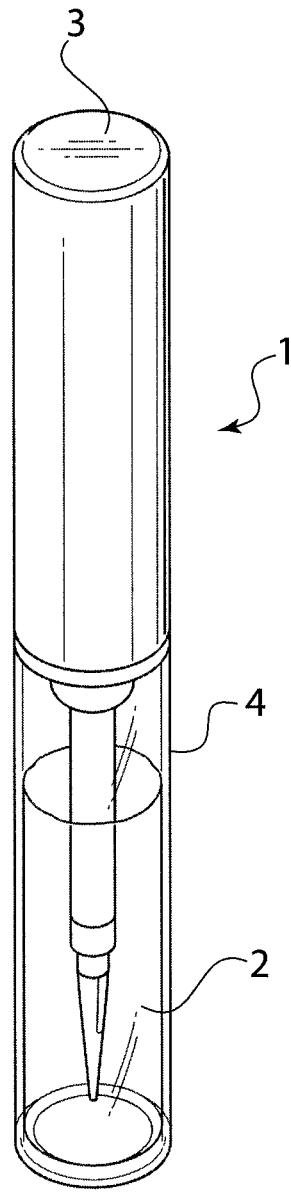
FIG. 1 depicts a type of container suitable for storing and dispensing a composition according to the present invention.
Figure 2:
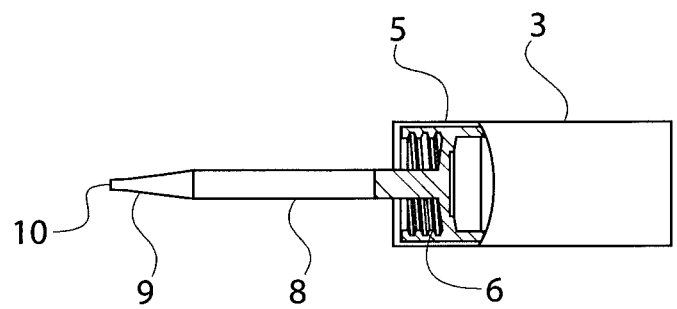
FIG. 2 depicts a pinpoint applicator.
Figure 3:
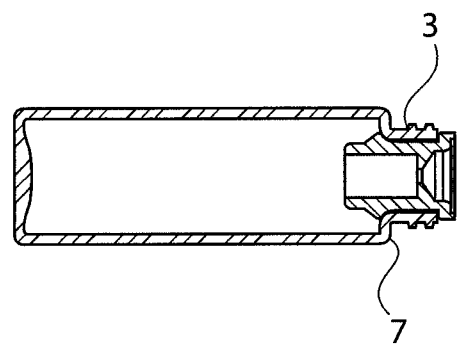
FIG. 3 shows the receptacle of the container in more detail.

All percentages mentioned herein are percentages by weight unless otherwise indicated. All patents or patent applications referred to herein by number are incorporated by reference in their entirety. The term "liquid" when used to describe the polymeric material means that the polymeric coating material composition is a pourable liquid at room temperature (25° C.).

A. The Composition

The composition of the invention comprises a liquid polymeric coating material that hardens to a water resistant, water vapor permeable, adherent and conformable solid film when applied to skin, and at least one skin whitening active.

1. Polymeric Coating Material

The polymer used in the composition of the invention is initially liquid at ambient temperature, but curable or dryable upon exposure to ambient air to form a solid, water resistant, adherent film that is also conformable to skin. The type of film formed on skin after air curing most resembles the so-called "liquid bandage" which is a liquid film which dries to a solid adherent film when applied to skin. The film conforms to skin and typically remains adherent to the skin for an extended period of time through showering, swimming, and normal outdoor activities. At the same time the polymer film will not adhere to substrates other than skin. Thus the coating will remain adherent and conformable to the skin surface but will not exhibit sufficient tack or adhesiveness to collect dust, or stick to clothing, or other objects that may contact the film.

The polymer coating material may be present in the composition in amounts ranging from 1 to 99.9%, preferably from about 1 to 95%, more preferably from about 1 to 75%. In one preferred embodiment the polymeric coating material when applied to the skin in a thickness from 0.0005 to 0.010 inches will have a moisture vapor transmission rate of 100 to 1,000 gm/m²/day. Suitable polymers for use in the composition include, but are not limited to, the following:

(a). Composite Siloxane Polymers

Suitable composite siloxane polymers include those which are the reaction product of a silanol endblocked polydimethylsiloxane and a silicate resin. The polymer is the reaction product of a siloxane resin comprising at least T or Q units or both and optionally M or D units, and a diorganosiloxane. Such polymers may be synthesized according to the methods set forth in U.S. Pat. No. 4,584,355.

The term "M" unit means a monofunctional siloxy unit having the general formula:

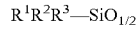

$$R^1R^2R^3\text{—SiO}_{1/2}$$

wherein $R^1$, $R^2$, and $R^3$ are each independently C1-30, preferably C1-12, more preferably C1-4 straight or branched chain alkyl or alkoxy, which may be substituted with phenyl or hydroxy groups, carboxylic acids.

The term "D" unit means a difunctional siloxy unit having the general formula:

$$R^1R^2\text{SiO}_{2/2}$$

wherein $R^1$ and $R^2$ are as set forth above with respect to the "M" unit definition.

The term "T" unit means trifunctional siloxy unit have the following formula:

$$R^1SiO_{3/2}$$

wherein $R^1$ is as set forth above.

The term "Q" unit means a quadrifunctional siloxy unit having the following formula:

$$SiO_{4/2}$$

The siloxane polymer may be made by hydrolysis of silane monomers, preferably chlorosilanes. The chlorosilanes are hydrolyzed to silanols and then condensed to form siloxanes. For example Q units are often made by hydrolyzing tetrachlorosilanes in aqueous or aqueous/alcoholic media to form $Si(OH)_4$ units. This hydroxy substituted silane is then polymerized with silanol substituted units such as diorganosiloxanes.

In the preferred embodiment of the invention the polymer is made according to the following reaction:

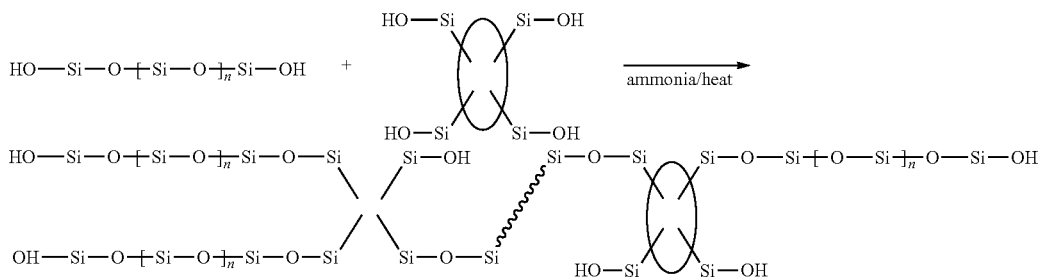

Most preferred are polymers sold by Dow Corning Corporation under the trade names 7-4405 which has the CTFA name dimethicone silylate. The polymer may be supplied to the composition in the form of a solution or dispersion in volatile solvents such as linear silicones or paraffinic hydrocarbons. Most preferred is where the polymer comprises Dow Corning 7-4405 Cosmetic Fluid, which is a mixture of 40 parts dimethicone silylate and 60 parts isododecane. In this case, the composition comprises from about 1-35%, preferably from about 1-30%, more preferably from about 3-20% by weight of the total composition of the polymer material.

(b). Copolymers of Siloxanes and Ethylenically Unsaturated Monomers

Also suitable are copolymers of siloxane and one or more ethylenically unsaturated monomers. Examples include the copolymers set forth in U.S. Pat. No. 5,103,812 which are polymerized from vinyl alkylsiloxane monomers and acrylic acid, methacrylic acid or their simple C1-10 straight or branched chain alkyl esters. Further examples of ethylenically unsaturated monomers include methyl methacrylate, methyl arylate, tetrahydrofurfuryl methacrylate, cyclohexyl acryalte, tetrahydrofurfuryl acrylate, n-lauryl acrylate, n-lauryl methacrylate, 2-phenoxyethanol acrylate, 2-phenoxyethanol methacrylate, isodecyl acrylate, isodecyl methacrylate, isooctyl acrylate, isooctyl methacrylate, isobornyl acrylate, isobornyl methacrylate, 2-butoxyethyl acrylate, n-butyl acrylate, n-butyl methacrylate, ethyl acrylate, ethyl methacrylate, dimethyl itaconate, di-n butyl itaconate, 2-ethylhexyl acrylate, 2-ethylhexyl methacrylate, furfuryl methacrylate, methyl acrylate, alpha methyl styrene, styrene, p-t-butyl styrene, 4-methoxystyrene, n-octadecyl acrylate, n-octadecyl methacrylate, 2-phenylethy methacrylate, n-tridecyl methacrylate, vinyl benzoate. Any of such monomers may be substituted with halogens such as chlorine, fluorine, and the like.

The above mentioned monomers may be reacted with vinyl alkylalkoxysilanes having the formula:

$$CH_2=C(R^1)COOR^2SiR^3R^4R^5$$

wherein $R^1$ is H, $CH_3$, or $CH_2$—COOR'; $R^2$ is a C1-10 alkyl or $CH_2CH(OH)CH$; $R^3$, $R^4$, and $R^5$ are O—$Si(Y)_3$, or C1-10 alkyl; wherein at least one of $R^3$, $R^4$, or $R^5$ is O—$Si(Y)_3$; and wherein Y is C1-10 alkyl, $OSi(Z)_3$ or $R^2OOC(R^1)C=CH_2$, wherein Z is C1-6 alkyl, aryl, and R' is $R^2SiR^3R^4R^5$.

Particularly preferred is where the vinylalkylalkoxysilanes are:
3-methacryloyloxypropyltris(trimethylsiloxy)silane;
3-methacryolyoloxypropylpentamethyldisiloxane;
3-methadryloylosypropylbis(trimethylsiloxy)methylsilane;
3-acryloyloxypropylmethylbis(trimethylsiloxy)silane
3-acryloxypropyltris(trimethylsiloxy)silane And the ethylenically unsaturated monomers are one or more of acrylates, methacrylates, isooctylacrylate, and combinations thereof.

(c). Cyanoacrylate Homo- or Copolymers

Also suitable as the polymeric material are cyanoacrylate homo- or copolymers. Examples include polymers disclosed in U.S. Pat. Nos. 6,183,593; 8,217,110. The cyanoacrylates may be substituted with C2-30 straight or branched chain alkyl groups, e.g. butyl cyanoacrylate, octylcyanoacrylate, and the like. An example of a cyanoacrylate monomer repeat unit that may be suitable is:

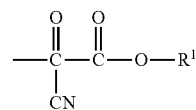

wherein $R^1$ is a C1-10, preferably C8, straight or branched chain alkyl which may be substituted with halogens (Cl, F, Br, I, etc.)

The cynaoacrylate monomer may be polymerized with one or more monomers such as vinyl pyrrolidone; acrylic acid, methacrylic acid or their simple esters; siloxanes; vinyl siloxanes, and the like.

2. Skin Whitening Active

The composition also contains at least one skin whitening active ingredient. Specifically, the skin whitening ingredient is present in amounts ranging from about 0.01 to 35%, more preferably from about 0.1 to 15%, more preferably from about 0.1 to 2.0% by weight of the total composition.

Suitable skin whitening actives include, but are not limited to, those identified as skin bleaching agents in the CTFA Cosmetic Ingredient Dictionary and Handbook, 2006. Ingredients include but are not limited to dimethylmethoxy chroman palmitate, *Tricholoma matsutak, Cornus controversa* extract, *Curcuma longa* extract, *Glycyrrhiza glabra* extract, 3,3',4',7-tetrahydroxyflavone, *Artocarpus lakucha* extract, *Ilex paraguariensis* Leaf Extract, *Cynara scolymus* Leaf Extract, creatine ascorbate, 4,6,4'-Trihydroxyaurone, *Cordyceps sinensis* extract, Mycelia, *Poria cocos, Sclerotium, Panax ginseng* root, *Ginkgo biloba* extract, *Perilla frutescens, Citrus reticulate, Polygonum cuspidatum,* rhizome, I-copper/zinc/glycine, 4-hydroxybenzoate propionate, 4-hydroxybenzoate acetate, Safflower oil, Apricot extract, *Zingiber jujube* extract, *Palmaria palmata* extract, hexylresorcinol, phenethyl resorcinol, kojic acid, hinokitiol, *lactobacillus* extract, *Morus alba* root extract, niacinamide, resveratrol, resveratrol triphosphate, wheat germ extract, sulforaphane, glabridin, amentoflavone, arbutin, Hibiscus rose extract, hydroxyresveratrol, *Prunus mume* extract, Sunflower extract, curcumin, *Lycium chinense, Cornus officinalis* extract, *Shizandra chinense, Morus alba* bark, *Rubeas coreanus, Pinus korajensis, Prunus tomentosa, Juglans regia* (walnut) seed extract, *Pyrus malus* extract, *Camellia sinensis* extract, *Cucumis sativas* extract, *Scutellaria baicalensis* extract, and so on. Also useful are mixtures of botanical extracts sold under the tradenames Phyto white (mixture of water, butylene glycol, *Cornus officinalis* extract, *Shizandra chinense, Morus alba* bark, *Rubeas coreanus, Pinus korajensis, Prunus tomentosa,* and *Juglans regia* (walnut) seed extract) and Phytolight (a mixture of water, propylene glycol, butylenes glycol, *Pyrus malus* extract, *Camellia sinensis* extract, *Cucumis sativas* extract, and *Scutellaria baicalensis* extract).

3. Other Ingredients

The composition of the invention may contain other ingredients including but not limited to those set forth herein.

(a). Oils

The composition preferably contains one or more oils that may be volatile or nonvolatile. Such oils may be present in amounts ranging from about 0.1 to 75%, preferably from about 0.5 to 70%, more preferably from about 1 to 50% by weight of the total composition.

Volatile oils include cyclic silicones having the general formula:

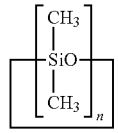

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

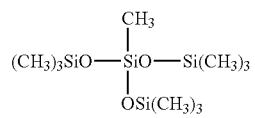

Methyl trimethicone may be purchased from Shin-Etsu Silicones under the tradename TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to those set forth herein.

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

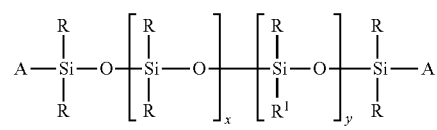

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

(b). Particulates

The composition preferably contains particulates in amounts ranging from 0.01 to 80%, preferably from about 0.1 to 70%, more preferably from about 0.5 to 65%.

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

In one preferred embodiment of the invention the composition contains a mixture of pigments and powders in an amount sufficient to cause the composition to match the surrounding skin when applied to the hyper pigmented spots.

(c). Surfactants

The composition preferably contains one or more surfactants. Surfactants are preferably nonionic silicone or organic surfactants, and may be present in amounts ranging from 0.1 to 40%, preferably from about 0.5 to 35%, more preferably from about 0.5 to 30%. Examples of surfactants.

(i). Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

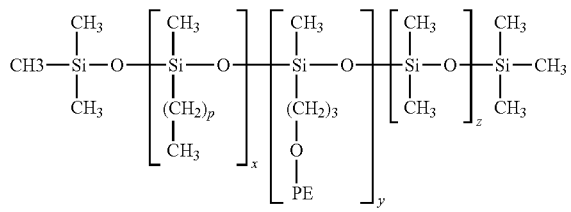

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236, 986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

(d). Montmorillonite Minerals

The composition may also contain one or more structuring agents such as natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like. Suggested ranges are from about 0.1 to 25%, 0.1 to 20%, more preferably from about 0.5 to 15% of the composition.

The composition may contain other ingredients such as preservatives, antioxidants, vitamins, and the like.

Preferred embodiments of the invention include a composition comprising:

A polymeric coating material which is dimethicone sylilate, a volatile oil which is isododecane, a non-volatile oil which is dimethicone, a mixture of titanium dioxide and iron oxides a silicone surfactant which is Cetyl PEG/PPG 10/1 dimethicone, PEG_10 dimethicone, or mixtures thereof A skin whitening ingredient.

Another embodiment of the composition contains:

A polymeric coating material which is octyl cyanoacrylate, a mixture of titanium dioxide and iron oxides A skin whitening ingredient.

Another embodiment of the composition contains:

B. The Method

In the method of the invention the composition is applied to the hyper pigmented spots on the skin at least once per day, or more often if necessary. The composition may be applied to any skin surface where there are hyper pigmented spots, including face, hands, back, arms, etc. Due to the adherent nature of the composition, it will remain on the spots to which it is applied over a time period from 12 to up to 72 hours. The placement of the composition containing the skin whitening agent on the spot itself and its adherence to skin for an extended period of time (for 4 to 60 days) will whiten the spot very effectively. The composition remains on the spot more effectively than applying a skin whitening composition to the skin from time to time. When the composition is applied over an extended period of time, the treatment is much more effective.

C. The Kit

The invention also comprises a kit for use in whitening hyper pigmented spots on skin comprising:

A receptacle having a closure and an applicator, and stored within the receptacle a liquid polymeric coating material that, upon exposure to ambient air and moisture in skin, will harden to a water resistant, water vapor permeable, adherent and conformable solid film when applied to skin, and at least one skin whitening active.

Figure 4:
FIG. 4 depicts the applicator tip of the pinpoint applicator.

One embodiment of the kit according to the invention is set forth in FIGS. 1-4. FIG. 1 depicts a type of container 1 suitable for storing and dispensing the composition 2. The container 1 has a cap 3 and a receptacle 4. Cap 3 is preferably affixed to receptacle 4 with threads 5 which mate with threads 6 on neck 7 of receptacle 4. A rod 8 extends from cap 3 and has an applicator 9 at the distal end thereof. Preferably the applicator 9 is what is referred to as a pinpoint applicator 10 as depicted in FIG. 4. This enables application of the composition specifically to the hyper pigmented spots, which are often small and discrete on the treatment surface. Pinpoint applicator preferably has an application surface that ranges from 5 to 50 mm in surface area, more preferably from 5 to 25 mm. Pinpoint applicator may be made of silicone or thermoplastic material such as polyurethane, polyethylene, polypropylene, and so on, and may or may not be deformable. The pinpoint applicator may also be flocked.

The invention is further described in connection with the following examples which are set forth for the purposes of illustration only.

Example 1

A composition for treating hyper pigmented spots on skin was prepared as follows:

| Ingredient | % by weight |
| --- | --- |
| Titanium dioxide | 41.67 |
| Isododecane | 14.80 |
| Dimethicone | 12.76 |
| Dimethicone silylate | 9.76 |
| Iron oxides (CI77492) | 5.93 |
| Polymethylmethacrylate | 3.73 |
| Tetrahexadecyl ascorbate | 3.00 |
| Phenyl trimethicone | 2.00 |
| Iron oxides (CI77491) | 1.18 |
| Cetyl PEG/PPG 10/1 dimethicone | 1.00 |
| Triethoxycaprylyl silane | 0.92 |
| Disteardimonium hectorite | 0.90 |
| PEG-10 dimethicone | 0.70 |
| Lecithin | 0.50 |
| Sorbitan sesquioleate | 0.50 |
| Caprylyl glycol | 0.30 |
| Skin whitening ingredient | 2.00 |
| Bisabolol | 0.10 |
| Propylene carbonate | 0.07 |
| Iron oxides (CI77499) | 0.02 |

The composition was prepared by combining the ingredients and mixing well to form a viscous liquid which was stored in a container with air tight cap and a wand applicator with brush. The composition was applied to the volar forearm of test subjects, 0.10 grams. Upon drying a "liquid band-aid" was formed. Photographs were taken. The subjects were then instructed to undergo their normal daily routine with at least one showering and return for photographs at 24 and 48 hours. All of the test subjects agreed that the composition was virtually unchanged in both adhesion and color retention after 48 hours.

Example 2

A formula for treating hyper pigmented spots on skin was prepared as follows:

| Ingredient | % by weight |
| --- | --- |
| Titanium dioxide (CI77891) | QS100 |
| Dimethicone | 19.57 |
| Isododecane | 14.80 |
| Dimethicone silylate | 9.20 |
| Iron oxides | 4.95 |
| Phenyl trimethicone | 2.00 |
| Triethoxycaprylyl silane | 1.00 |
| Cetyl PEG/PPG-1 dimethicone | 1.00 |
| PEG-10 dimethicone | 0.70 |
| Disteardimonium hectorite | 0.63 |
| Sorbitan sesquioleate | 0.50 |
| Lecithin | 0.50 |
| Caprylyl glycol | 0.30 |

-continued

| Ingredient | % by weight |
| --- | --- |
| Tocopheryl linoleate/oleate | 0.20 |
| Linoleic acid | 0.20 |
| Bisabolol | 0.10 |
| Tetrahexyldecyl ascorbate | 0.10 |
| Propylene carbonate | 0.04 |
| Glycyrrhiza glabra extract | 0.10 |

The composition was prepared by combining the ingredients and mixing well to form a viscous liquid.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A method for whitening discrete hyper pigmented spots on skin by applying to the discrete spots in need of whitening and not to the surrounding non-hyper-pigmented skin a liquid pigmented treatment composition comprising at least one skin whitening active in a polymeric coating material comprising 1-35% dimethicone silylate; from 1-50% of a volatile solvent selected from the group consisting of isododecane, dimethicone and mixtures thereof; from 1-50% of a non-volatile silicone oil having a viscosity of 20 to 200,000 cst at room temperature; from about 0.1 to 40% of a silicone surfactant; from about 0.1 to 15% of a quaternized montmorillonite mineral; and from 0.5 to 65% titanium dioxide in combination with pigments that, upon exposure to ambient air and moisture in skin, hardens to a water resistant, water vapor permeable, conformable solid film that colors the spots so they are shade matched with the surrounding non-hyperpigmented skin and remains unchanged in adherence and color to the spots for 24 hours after application and is thereafter applied to the spots every 12 to 72 hours to color the spots to shade match them to the surrounding untreated skin while whitening the treated spots over time while the pigmentation of the untreated surrounding non-hyperpigmented spots remains unchanged.

2. The method of claim 1 wherein the treatment composition is re-applied after the first application for a time sufficient to cause the discrete hyper-pigmented spots to whiten to match the untreated surrounding non-hyperpigmented skin.

3. The method of claim 2 wherein the treatment composition is applied for 4 to 60 days.

4. A method for whitening discrete hyper pigmented spots on skin by applying to the discrete spots in need of whitening and not to the surrounding non-hyper-pigmented skin, a treatment composition comprising a skin whitening active in a liquid polymeric coating comprising dimethicone silylate, isododecane, dimethicone, phenyl trimethicone, dimethicone copolyol, a quaternized montmorillonite mineral, polymethylmethacrylate, and titanium dioxide containing pigments, that, upon exposure to ambient air and moisture in skin hardens to a water resistant, water vapor permeable, adherent, conformable solid film that colors the spot to shade match the surrounding untreated non-hyperpigmented skin wherein the adherence of the treatment composition to the spots remains unchanged for 24 hours and the treatment composition is re-applied every 12 to 72 hours thereafter for a time sufficient to cause the treated discrete hyper-pigmented spots to match the surrounding non-hyperpigmented skin and whiten the spots over time while the untreated surrounding non-hyperpigmented skin remains unchanged.

5. The method of claim 4 wherein the treatment composition is applied every 12 to 72 hours for a period of 4 to 60 days.

6. A kit for whitening discrete hyper pigmented spots on the hands comprising:
a receptacle having a closure with a cap and extending rod having affixed at the distal end a deformable pinpoint applicator with an application surface of a size that permits application of a treatment composition to discrete hyperpigmented spots on the hands and not surrounding non-hyperpigmented skin, and stored within the receptacle a treatment composition comprising at least one skin whitening active in a polymeric coating material comprising 1-35% dimethicone silylate; from 1-50% of a volatile solvent selected from the group consisting of isododecane, dimethicone and mixtures thereof; from 1-50% of a non-volatile silicone oil having a viscosity of 20 to 200,000 cst at room temperature; from about 0.1 to 40% of a silicone surfactant: from about 0.1 to 15% of a quaternized montmorillonite mineral; and from 0.5 to 65% titanium dioxide in combination with pigments that, upon exposure to ambient air and moisture in skin, hardens to a water resistant, water vapor permeable, adherent and conformable solid film that colors the spot so they are shade matched with the surrounding non-hyperpigmented skin; wherein the adherence and color of the treatment composition to the spots on the hands remains unchanged for one day after application.

7. The kit of claim 6 wherein the applicator is a brush.

8. The kit of claim 6 wherein the pinpoint applicator is made from silicone or a thermoplastic material selected from the group consisting of polyurethane, polyethylene, or polypropylene.

9. The kit of claim 6 wherein the pinpoint applicator is made from thermoplastic polyurethane.

10. The kit of claim 9 wherein the pinpoint applicator is deformable.

11. The kit of claim 9 wherein the pinpoint applicator is flocked.

12. The kit of claim 6 wherein the applicator has an application surface from 5 to 25 millimeters in diameter.

* * * * *